United States Patent [19]

Koenhen et al.

[11] Patent Number: 5,240,862
[45] Date of Patent: Aug. 31, 1993

[54] PROCESS AND DEVICE FOR THE SEPARATION OF A BODY FLUID FROM PARTICULATE MATERIALS

[75] Inventors: Dirk M. Koenhen, Enschede; Johan J. Scharstuhl, Hengelo, both of Netherlands

[73] Assignees: X-Flor B.V.; Primecare B.V., both of Enshede, Netherlands

[21] Appl. No.: 328,063

[22] Filed: Mar. 23, 1989

[30] Foreign Application Priority Data

Mar. 29, 1988 [NL] Netherlands ............................ 8800796

[51] Int. Cl.⁵ .................... G01N 1/18; G01N 31/22; B01L 11/00
[52] U.S. Cl. ................................. 436/178; 436/170; 436/177; 422/56; 422/58; 422/60; 422/101; 210/500.24; 210/500.27
[58] Field of Search ..................... 210/500.23, 500.27, 210/195.1, 500.1, 500.21, 500.24; 436/170, 169, 95, 177, 178; 435/11; 422/586, 58, 60, 101, 61; 427/245

[56] References Cited

U.S. PATENT DOCUMENTS

| | | | |
|---|---|---|---|
| 4,066,512 | 1/1978 | Lai et al. | 530/356 |
| 4,280,909 | 7/1981 | Deutsch | 210/500.21 |
| 4,477,575 | 10/1984 | Vogel et al. | 422/56 |
| 4,824,639 | 4/1989 | Hindenbrand et al. | 422/56 |
| 4,863,603 | 9/1989 | Lehmann et al. | 210/489 |
| 4,870,005 | 9/1989 | Akiyoshi et al. | 436/169 |
| 4,876,067 | 10/1989 | Deneke et al. | 436/169 |
| 4,895,704 | 1/1990 | Arai et al. | 436/169 |
| 4,906,375 | 3/1990 | Heilmann | 210/500.23 |
| 4,983,288 | 1/1991 | Karbachsch et al. | 210/490 |
| 4,987,085 | 1/1991 | Allen et al. | 422/57 |
| 4,994,238 | 2/1991 | Daffern et al. | 422/57 |

FOREIGN PATENT DOCUMENTS 8400015 1/1984 World Int. Prop. O. .

OTHER PUBLICATIONS

Primetest Life Style Diagnostics Brochure, Prime Care b.v., date unknown.

*Primary Examiner*—James C. Housel
*Assistant Examiner*—Jan M. Ludlow
*Attorney, Agent, or Firm*—Brooks Haidt Haffner & Delahunty

[57] ABSTRACT

The present invention deals with a process and device for the separation of a body fluid from particulate materials in the fluid to be used for a chemical analysis of the fluid components. The process and device are in particular suitable for the separation of plasma from whole blood. Furthermore the present invention relates to a testing kit for the above mentioned separation and analysis purposes. The device has a collector membrane of defined capacity which intimately contacts the small pore side of a separator membrane having asymmetric pores passing through it permitting the application of a body fluid to the large pore side of the separator membrane.

14 Claims, 1 Drawing Sheet

PROCESS AND DEVICE FOR THE SEPARATION OF A BODY FLUID FROM PARTICULATE MATERIALS

A process and device for the separation of a body fluid from particulate materials in said fluid, in particular plasma from whole blood, to be used for a chemical analysis and testing kit for said separation and analysis.

BACKGROUND OF THE INVENTION

The present invention relates to a process for the separation of a body fluid from the particulate materials present in said fluid, in particular plasma from whole blood, to be used for a chemical analysis wherein a small amount of body fluid is contacted with a membrane or composite of membranes, said body fluid mi7grates into said membrane or composite whereas said particulate materials and non-migrated body fluid are retained and said migrated fluid is used for analysis purposes. Furthermore the present invention relates to a device for the separation of a body fluid from the particulate materials present in said fluid, in particular plasma from whole blood, comprising an inert solid support to which a membrane or composite of membranes is attached. Finally the invention relates to a testing kit for separation and chemical analysis of the components of a body fluid.

Although the present invention related to the separation of a body fluid from the particulate materials present therein and to a chemical analysis of said body fluid in general, such as lymph, urine and other body fluids the present invention will be further disclosed and illustrated by means of whole blood as a body fluid.

In view of diagnostic and therapy and for controlling of certain body functions there is since many years a need for analysis of body fluids in order to analyse the presence and/or concentration of a certain substance in said fluid. In particular blood is a frequently examined medium, which may lead to indications for several body functions and body processes. Since blood is a troubled medium because of the several particulate materials present therein, such as thrombocytes (blood platelets), erythrocytes (red blood cells) and leucocytes (white blood cells) whole blood is a troublesome medium for chemical analysis, since such particular materials do interfere with the usual analytical chemical techniques used for the determination of the presence and concentration of certain components. Accordingly several methods have been developed for the separation on the one hand of particulate materials and on the other hand of the plasma or serum from whole blood. For the somewhat larger amounts of blood (in the order of millimeters and more) many methods have been developed, which are mostly based on the centrifugation principle, wherein the blood cells are precipitated from the plasma or serum by means of the centrifugal force. However such methods usually do require complicated adjustments in order to recover the plasma or serum without the particulate materials. Another disadvantage of such techniques is that they require greater amounts of blood, which should be taken off by means of a venous puncture. Because of the above mentioned facts such methods are only used in the clinical chemical laboratory.

By the increasing demand for analysis data of body fluids, in particular blood, and by the increasing need for quick and simple analysis methods means are developed which only require a slight amount of blood, e.g. a drop of blood, obtained via a finger puncture. Such means exist usually in the form of a strip of an inert material, to which several layers are applied, which are able to achieve a separation between the particulate materials of the blood on the one hand and plasma or serum on the other hand, so that the particulate materi7als are retained in or on one or several of the upper layers, whereas the clear plasma is collected in the layers thereunder. In one or several of these layers reagents may be introduced. There reagents do simultaneously or after each other get in contact with the plasma and therefore they may react with the component to be determined. Because of this reaction a change in a physical property does occur, which change is a measure for the concentration of the substance to be determined, which change is observed visually or by means of suitable device, which leads to a semi7quantitative and quantitative result respectively.

Accordingly the U.S. Pat. No. 3,092,465 discloses the coating of a strongly sucking test paper, which is provided with a semi7permeable membrane for the determi7nation of the blood sugar content. Herein blood is applied to the semi7permeable membrane, through which membrane only water and glucose pass but other bigger molecules such as hemoglobin or proteins are retained. Said glucose and water are taken up in the paper layer, which is provided with suitable reagents. The changing colour such obtained is then measured visually or remission- or reflection photometrically. This change in colour is observed through the semi7permeable membrane, which has therefore to be transparent and from which the disturbing particulate materials should be removed by means of washing or wiping. Such a method is only suitable for the determination of substance having small molecules.

Further it is known from German "Offenlegungsschrift" 1,598,153 to use a film which may swell up in water, which contains reagents. The components which are dissolved in the blood penetrate into the semi7 permeable film, whereas the particulate materials are retained. This method has however similar disadvantages as the method which is disclosed in U.S. Pat. No. 3,092,465.

In order to improve such systems having semi-permeable membranes or films, several systems have been developed in order to separate particulate materials from blood to recover plasma or serum. Accordingly German "Offenlegungsschrift" 2,222,951 discloses a testing device for the determination of the enzyme activity in blood, wherein several different layers are arranged after each other, whereas one or several of these layers do function as a filter. Herein the upper two layers are porous glass fibre discs, which act as prefilter in order to retain particulate materials such as white blood cells, in order to prevent clogging of the underlying membrane filter disc. The membrane filter disc acts as a filter for removing the red blood cells and other particles. Finally under said membrane filter disc there is provided a disc of cellulose acetate. Each of the separate discs provide distinctive test zones. The colour change which is obtained by such analysis method is observed visually. The disadvantage of such method is that the plasma only very slowly and in slight amounts may penetrate into the membrane filter, whereas this membrane filter may be clogged easily, which means that said plasma slowly and unequally penetrates into the reaction layer. Furthermore German "Offenlegungsschrift" 2,922,958 discloses a multi layer element, having at least four layers consisting of an upper filter layer, a water impermeable layer thereunder having one or more orifices, then an expanding layer and finally a reagent layer. As filter layer use is made of one or several membrane filters, whereas the porous expanding layer may also be a membrane filter. It is stated that the expanding layer is weak and fragile (see page 15, sub 5) so that this layer should be sandwiched between other layers in order to prevent problems during handling. Such a multi layer element has similar disadvantages as mentioned in the German "Offenlegungsschrift" 2,222,951.

The above discussed methods wherein on the one hand use is made of semi-permeable membranes and on the other hand use is made of membrane filters (porous membranes) did not lead to fully satisfactory results. A further development of such methods is disclosed in the European patent application 45476, wherein it is suggested to apply a layer of glass fibres in the form of a disc onto the known testing devices as cover. The glass fibre disc retains the particulate materials from the blood and enables to pass serum or plasma into the layers thereunder. As disadvantages of such a system are mentioned (see European patent application 133895, page 3) the relatively high dead volume of this glass fibre disc as well as the fact that such a disc is not able to retain the erythrocytes completely, so that blood colour penetrates into the reaction zone which disturbs the reaction. Therefore in the last mentioned European patent application a substrate is suggested which should be contacted with blood and which substrate together with blood should be passed through a specific filter disc, so that the separated plasma may be recovered in the layers thereunder.

Finally according to the methods disclosed in the European patent application Nrs. 0154839 and 0175990 the blood sample is applied to that side of the membrane where the pore size is the smallest (the so-called smooth surface of the membrane). This has as serious disadvantage that the small pores are clogged by the blood parti7 cles such as thrombocytes, erythrocytes, leucocytes and coagulates thereof, resulting in the fact that only very slight amounts of plasma penetrate into the membrane. This means that the reaction time is too long with the risk that the determination is inaccurate. (In connection with the above mentioned disadvantages reference is made to European patent application No. 0045476 in the name of Boehringer Mannheim GmbH, page 2, lines 14 through 20).

Another disadvantage is that the blood has to be wiped off from the smooth surface of the membrane, whereby damaging of the erythrocytes is practically unavoidable, which means that the desired colour reaction is disturbed.

In conclusion there are several methods and testing devices available, which are also known as quick diagnostics, which may be used for the analysis of a slight amount, e.g., a drop, of whole blood. However in case of the use of semi-permeable membranes there is not obtained the total plasma or serum, but only the components to be determined with a small molecule size, whereas in using membrane filters usually complicated provisions should be taken in order to safeguard a proper process. Furthermore it should be noted that frequently cloggings occur and that the plasma or serum only slowly passes through such membranes. The recent developments in this art make use of other filter discs than membrane filters. Except the above mentioned disadvantages and shortcomings each of the above mentioned methods relate to "dry" analysis methods. This means that the result, usually a colour change, should be evaluated visually or by means of reflection photometric. A visual method is however not quantitative, whereas a reflection photometric method requires a relatively expensive measuring device and make high demands of the test systems. Further the known test systems are usually provided with swellable reagent layers, so that it is often difficult to obtain a reproduceable result, since a drop of blood, in particular when said drop of blood should be applied on such a test system, mostly does not lead to a reproducable result. Furthermore the long time period which is required for the plasma to penetrate in such systems may result in the fact that the blood begins to coagulate, resulting in clogging of the entire system.

Therefore there is a need for a simple and cheap method and device for the chemical analysis of components of body fluids, wherein use is made of a drop or a small amount of such a liquid, wherein the above mentioned disadvantages are eliminated. Furthermore there is also need for a quick, simple and accurate "wet" analysis of such fluids, wherein relatively cheap analysis apparatus may be used, such as e.g., colorimeters or photometers, which means that such a method is accessible for routine examinations, not only in clinical laboratories, but also by general practitioners and so on.

SUMMARY OF THE INVENTION

Surprisingly it has been found that by making use of special membranes said goals may be achieved. Therefore the process for the separation of a body fluid from the particulate materials in said fluid, in particular plasma from blood, by contacting a slight amount of body fluid with a membrane or composite of membranes, wherein the body fluid penetrates into the membrane or composite under retaining of any particulate materials and not-penetrated body fluid, wherein the penetrated fluid is used for analysis purposes, according to the invention is characterized in that one or. more hydrophilic microporous membranes, at least one of which (the collector membrane) has a defined pore volume, is or are used, wherein the absorbed, defined amount of body fluid which is free of the particulate material, is used for a semi-quantitative or quantitative, dry or wet chemical analysis in order to determine one or more of its components.

By treating in this way a slight amount (such as a drop) of body fluid, one achieves quickly a separation between the particulate materials in the body fluid and the remaining of the fluid. It is to be noted that the process equally may be used for body fluids such as plasma or serum, urine etc. from which the particulate materials have been removed already, because of the hydrophilic properties of the microporous membranes the liquid part of the body fluid penetrates easily and quickly into the pores, wherein such an amount of fluid is taken up that the pores are filled up. In the prior art generally use is made of hydrophobic membranes or films or paper discs which have been made hydrophobic. Because in the present invention one or more membranes are used, of which at least one (the collector membrane) has a defined pore volume, it is possible to take up into the membrane a properly determinable defined amount of fluid. According to the present invention two objects are achieved simultaneously, to wit the separation of the particulate materials and the quantification of the absorbed fluid. This quantified amount of fluid may then be used according to two manners for the chemical analysis, to wit a dry and a wet analysis, which will be illustrated in more detail hereinafter. In particular the wet analysis is very advantageous, because said analysis enables to obtain quantitative results with the use of relatively cheap apparatus. Since the pore volume of the hydrophilic microporous membranes in the present process may be determined accurately, it is possible to obtain simply a quantitative result also in the dry analysis without special measures in order to obtain a defined amount of fluid sample. As mentioned before in the prior art generally use is made of swellable membranes or films, so that e.g., the body fluid should penetrate into the layer during a certain time in order to obtain an accurately determinable amount of absorbed fluid.

Since the total plasma/serum is recovered, it is according to the present process in principle possible to analyse each plasma/serum component. Some of the not limitative examples are: glucose, urea, cholesterol, proteines, lipides etc.

It should be understood that in the plasmaferesis, where the plasma is separated from the whole blood, use is made of microporous membranes. However this process relates to the recovery of greater amounts, wherein the plasma is pressed through the membrane under pressure. The microporous membranes, which are used in the plasmaferesis, are in the device in general already humidified which means that said membranes do not take up the plasma in a quantitative amount without any pressure.

As it will be clear from the above, in principle any hydrophilic microporous membrane may be used, provided that is has a defined pore volume. A category of membranes which appeared to be suitable in the process according to the invention is disclosed in the older not-prepublished European patent application 87201789.2. The hydrophilic microporous membranes disclosed in the above European patent application have the considerable advantage that the pore structure may be adjusted accurately, which means that the membranes may be tailored.

According to a preferred embodiment of the process of the invention a hydrophilic microporous membrane is used, which essentially consists of a hydrophobic polymer and a hydrophilic polymer, which hydrophilic polymer is fixed in or on the polymer matrix. As described in the European patent application 87201789.2 this fixation may be achieved by cross-linking the hydrophilic polymer in an essentially not-swollen state. For further details relating to the preparation of suitable membranes, reference is made to this European patent application.

It is particularly preferred an embodiment of the present process wherein a membrane is used in which the hydrophobic polymer is represented by polysulpone, polyether sulphone or polyetherimide, whereas the hydrophilic polymer is polyvinyl pyrrolidine.

A further preferred embodiment of the present process is characterized in that, after applying the slight amount of body fluid that part of the collector membrane to which/wherein the remained particulate materials are present and to which/wherein the non-absorbed fluid is present, is separated. By making use of a collector membrane, which may be separated in two zones, of which one zone contains the fluid residues and the other zone contains an accurately measurable of the absorbed fluid, the present process may be carried out by inserting the zone intended for the fluid residue in the body fluid to be analysed (e.g., blood or plasma or serum which is being received in a tube). The absorption zone and the fluid residue zone may be separated from each other. In order to accomplish this separation several methods are available which will be clear for the expert in the art.

A specially preferred embodiment of the process of the invention is characterized in that the slight amount of body fluid is applied onto a first surface of an additional hydrophilic microporous membrane (separator membrane), which is in contact with its opposite surface with the collector membrane in a separatable way, wherein the body fluid penetrates in such a way that the collector membrane or an accurately determined part thereof is saturated, whereupon the separator membrane together with the not-absorbed fluid on it and eventually the particulate material remained on it and/or therein are removed. In such a process use is made therefore of two membranes which are in mutual contact with each other, of which one, to wit the separator membrane, retains the particulate materials and the not-absorbed fluid, whereas the other, to with the collector membrane, is in contact with and absorbs the body fluid which is freed from the particulate materials by means of the separator membrane. However it is a condition for obtaining good results that the separator membrane and the collector membrane are in intimate contact with each other, which can be achieved by slightly pressing both membranes to each other. The time period which is required for the saturation of the collector membrane or an accurately determined part thereof varies between a few seconds to a few minutes dependent on the composition and structure of the membranes. The manner of how to contact the membranes with each other and the separation of these membranes from each other later is not critical and the various manner to achieve this will be clear to the expert.

Although symmetrical hydrophilic microporous membranes are suitable in the present process it is preferred to use at least one asymmetric hydrophilic microporous membrane. Upon an asymmetric membrane should be understood a membrane wherein the average pore size at one side of said membrane is larger than the average pore size at the opposite side of said membrane. The techniques for the preparation of asymmetric membranes are known in itself and they also may be used for the preparation of asymmetric hydrophilic microporous membranes. Asymmetric membranes have been used up till now with their relatively smooth side, having the smaller pores, directed to the fluid to be separated or purified. However according to the invention the slight amount of body fluid is applied on that side of the asymmetric membrane which contains the largest pores. The advantage of this is that the body fluid together with the particulate materials if any penetrate immediately into the pores, wherein the particulate materials are retained in the pores which are becoming gradually smaller, whereas the clear part of the body fluid penetrates quickly further. As disclosed above the particulate materials which are retained in and/or on the membrane may not be washed off or wiped off, rather it is to be removed together with that part of the membrane which is contaminated with the particulate materials (in case that a wet analysis is to be carried out). Since the fluid is spread out to all directions because of the open pore structure (which does not occur with the particulate materials), it is possible to separate that part of the membrane wherein the particulate materials are retained (that is where the membrane came into contact with the body fluid). A very suitable alternative of this process according to the invention is characterized in that an asymmetric separator membrane is used, wherein the surface having the smaller pore openings is in contact with the collector membrane. Accordingly in this variant two membranes are used from which the separator membrane which is used for the application of the body fluid is asymmetric. In this way the separator membrane is to be separated from the collector membrane instead of splitting up a collector membrane into two parts. In this last mentioned preferred embodiment it is very favourable to make use of an asymmetric collector membrane instead of splitting up a collector membrane into two parts. In this last mentioned preferred embodiment it is very favourable to make use of an asymmetric collector membrane too, from which the side with the smaller pore openings is in contact with the separator membrane. In this way the capillary suction of the clear body fluid into the collector membrane may occur optimally. It is self-explanatory that also several combinations of the here mentioned embodiments may be combined.

A further advantage of the present process lies in the possibility to provide a hydrophilic microporous membrane(s) with one or more reagents, which may be divided over one or more membranes. Accordingly one component which is to be analysed may be contacted with a reagent while in the membrane. It is preferred with the component(s) in the body fluid to be determined is/are reacted with the reagent(s) in or on the collector membrane. Said membrane in which the reagent containing body fluid is absorbed may be used according to one variant directly for a dry analysis. The change in the physical characteristics which is a result of the reaction is measured according to a method which is known in itself. This may occur e.g. visually, leading to a semi-quantitative result, or by means of a suitable measuring device such as remission or reflection photometers, leading to a quantitative result. The second variant will be illustrated hereunder.

As discussed in the introductory part the present process has the special advantage that the same is suitable for a wet chemical analysis of components in a body fluid. In this connection the present process is characterized in that the collector membrane or an accurate determined separable part thereof, together with the body fluid absorbed therein is introduced into a suitable reagent solution, the fluid which is absorbed in the membrane(part) is washed out, and the changed physical characteristics caused by the reaction are measured in a way which is known in itself. In this case it is possible to incubate the absorbed fluid first with a certain reagent, which may be collected in the collector membrane, as illustrated above. The absorbed fluid, eventually together with the reagent, is introduced into a suitable reagent solution after being washed out. In this way even a wet chemical analysis may be carried out, which consists of more than one separate steps. The reaction parameter, such as a colour change, may then be simply measured by means of a cheap apparatus. Because of the face that hydrophilic microporous membranes according to the invention may be washed out in the reagent solution quantitatively, it is possible to obtain very accurate results. A wet analysis of body fluid which is carried out in this way has not been disclosed in the literature as yet. However such a method is of very high value, because it may be carried out quickly and simply. It will be clear that the fluid which is collected into the collector membrane (part) may be freed from its particulate materials by means of the above disclosed manners.

When the present process is applied for the chemical analysis of components of blood, it may be advantageous to use a hydrophilic microporous membrane, which contains coagulation- and/or haemolysis inhibiting substance. As examples of coagulation inhibiting substance may be mentioned heparine and ethylene diamine tetra acetic acid. Examples of haemolysis inhibiting substances are disclosed in U.S. Pat. No. 3,552,928. These coagulation-and haemolysis inhibiting substances may be introduced into the membrane by means of methods which are known in itself.

According to a second feature the present invention relates to a device for the separation of a body fluid from the particulate materials present therein, which device comprises an inert solid support to which a membrane or composite of membranes is attached, characterized in that said device is provided with one or more hydrophilic microporous membranes, at least one of which (collector membrane) has a defined pore volume. Such a device or strip is particularly suitable for carrying out the above disclosed process of the invention. The term inert solid support means a support which is manufactured from a material which is inert with respect to the body fluid. Examples of such materials are the plastics and metals known for such applications. The shape of such a support is not critical, provided that during use the body fluid has to be able to come in contact with the or each of the membranes. Dependent on the situation whether a dry or wet chemical analysis is to be carried out, the membrane may be in contact with its one side with the support or the membrane should be free on both sides for absorption and washing out purposes. In case that the membrane which is attached to the support should be washed out, it is necessary that the support is inert too, with respect to the reagent solution.

As mentioned before the membrane may be a hydrophilic microporous membrane, provided that this has a defined pore volume. Suitable membranes consist essentially of a hydrophilic polymer and a hydrophilic polymer, which hydrophilic polymer is fixed in or into the polymer matrix. In this connection the hydrophobic polymer is preferably polysulphone, polyether sulphone or polyetherimide, whereas the hydrophilic polymer is polyvinyl pyrrolidone.

According to a preferred embodiment of the device according to the invention such device comprises besides the collector membrane furthermore a hydrophilic microporous membrane (separator membrane), which is in a separable contact with the collector membrane. The advantage of such a device is that because of the simple removable of that part of the support to which the separator membrane is attached, the separation between the fluid residue and the accurately determined absorbed amount in the collector membrane may be accomplished.

A further advantageous embodiment of the present device is characterized in that said device comprises an asymmetric hydrophilic microporous membrane. The advantages of such a membrane are mentioned in detail hereinbefore. The pore size of the asymmetric membrane at the side with the largest pores is in the range of 10 μm to 1 mm, whereas the pore size at the side with the smallest pores is in the range of 0.2 to 5 μm. It is in particular advantageous that by introducing the body fluid at the side having the largest pores, said fluid penetrates very quickly into the membrane, whereas the particulate materials are partly carried with the fluid, which particulate materials finally are retained by the decreasing size of the pores.

A device according to the invention which comprises a separator membrane and a collector membrane is preferably provided with an asymmetric separator membrane which is in contact with the collector membrane with its smallest pores. Such a device is furthermore preferably provided with an asymmetric collector membrane too, which is in contact with the separator membrane by its side having the smallest pores. The advantages of such embodiments of the present devices are illustrated with respect to the present process in more detail hereinbefore.

Another preferred embodiment of the device according to the invention is characterized in that the collector membrane is provided with an accurately determined separatable part. This is advantageous too when the collector membrane is used together with a separator membrane. It should be understood that because of the removal an accurately determined separatable part of the collector membrane, having a known pore volume, an accurate amount of absorbed fluid may be introduced into for instance a reagent solution, which enables the achievement of a quantitative measuring result. An additional advantage is that it is not required to fill up the entire membrane. The way of ascertaining of the separatable part as well as the way of removal thereof from the rest of the collector membrane, may be carried out in different manners, so that a detailed explanation will not be given. One of these possibilities will be discussed later.

Another embodiment of the device according to the invention is characterized in that the collector membrane or the accurately determined separatable part thereof is attached to an inert means which may be separated from the inert solid support. This attachment may be achieved by means of clamps, adhesives etc. Since the separatable inert means is removable from the inert solid support, the collector membrane or a part thereof may be isolated in a simple way and used further. It is preferred that the separatable means does clamp the collector membrane as well as optionally the separator membrane in or onto the inert solid support. Especially when both the collector membrane and the separator membrane are present, the contact between both membranes may be accomplished easily in this way.

As disclosed herein above with respect to the present process the hydrophilic microporous membrane contains a coagulation or haemolysis inhibiting substance in case that the device is to be used for chemical analysis of whole blood.

According to a final feature the present invention relates to a test kit for the separation and chemical analysis of the components of a body fluid, wherein the complete kit comprises one or more devices according to the present invention, one or more solid or liquid reagents in one or more suitable containers and optionally one or more solvents in separate containers. When a fluid residue of a membrane has to be removed it is preferred that said test kit also comprises a suitable packed isotonic solution which is present in a tissue in a saturated or not saturated state.

The terms collector membrane and separator membrane as used in the specification and claims refer firstly to the functions of the used membranes. The term collector membrane refers to the membrane having a defined pore volume and which contains the amount of fluid to be analysed. The term separator membrane is only used in order to indicate the use of an additional membrane, applied to a collector membrane, wherein the main function of the separator membrane is to retain the fluid residue which is not intended for chemical analysis. In case that only one membrane is used, this is indicated as collector membrane, although this membrane also has the function to separate the particulate materials from the rest of the fluid.

DETAILED DESCRIPTION OF THE INVENTION

Figure 1:
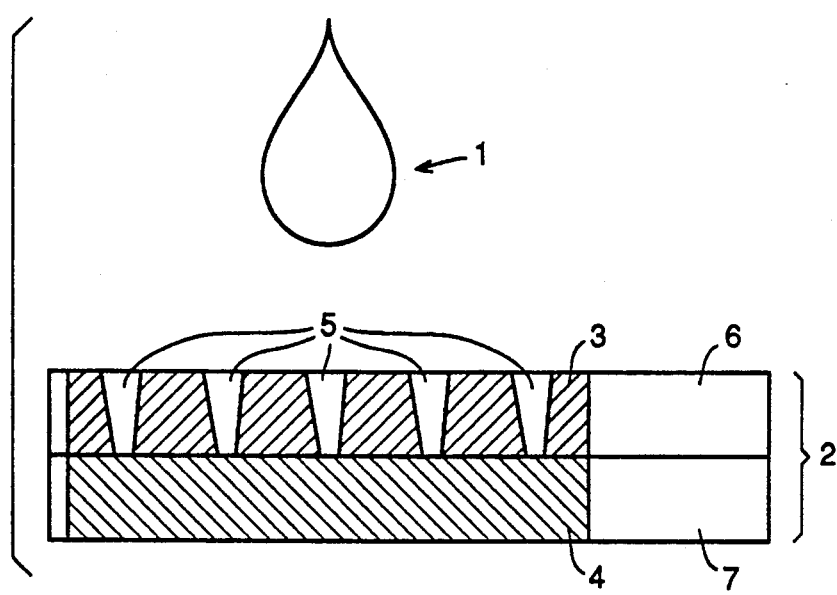
FIG. 1 is a schematic drawing illustrating the device of this invention. In this drawing a body fluid 1 is applied to a separator membrane 3 which abuts a collector membrane 4. The membranes are contained in a holder 2 having means for separating the collector and separator membranes. Each membrane has a handle 6 and 7. The collector membrane contains asymmetric pores 5.

An embodiment of the device for the separation of a body fluid from particulate materials in said fluid, in particular plasma from whole blood. This embodiment is provided with a handle and means for receiving the separator-and collector membrane. The separator membrane is indicated, whereas the collector membrane is not shown. Finally, the handle is of an inert removable means.

The separator membrane and the collector membrane may be inserted into the space of the means of the solid support. The other end of the removable means is connected with the handle. This means is provided with a grate which is breakably connected with the remaining part. Said means may be inserted together with the membranes and into the space of the support e.g., by means of a snap-closing, which enables that both membranes are pressed against the grate, so that between said membranes a suitable contact occurs. A weak spot enables removal of the grate of the remaining part, e.g., when the handle of the removable means is moved in an upward direction. The collector membrane comprises in this embodiment a zone, the size of which has been determined accurately and a surrounding zone, which both zones are connected to each other by means of a weak binding. By attaching one zone to the grate and by moving the handle in upward direction one zone will be separated from the other zone by breaking along the weak spots. The handle with the grate and the zone of the collector membrane attached thereto may be removed and used for chemical analysis. The collector membrane zone remain in the support. The shape of the membranes may be circular, square etcetera, whereas the weak spots may be circular or right angular. The weakening of the parts may be obtained in several manners.

A second embodiment of the device according to the present invention, which is indicated by handles and rooms for receiving the membranes. A hinge enables this device to fold out by moving the handles away from each other. The separator membrane is indicated by and is kept in position by means of grate.

In order to ensure a proper contact between the separator membrane and the collector membrane snap-closings are provided. The separator membrane is similarly supported by a grate. The left part of this embodiment may be separated from the right part by breaking or loosening of the hinge. The left part may then be further used for chemical analysis.

It should be understood that the above disclosed embodiments of the device according to the present invention only serve as example and that from that embodiment several alternatives may be developed which are also covered by the present invention.

The invention will be further illustrated by means of the following examples, to which the invention is not limited.

EXAMPLE I

In order to determine the contents and reproducability of the hydrophilic microporous membranes of the invention a known amount of cholesterol calibration serum type A of the R.I.V.M. of Bilthoven having a cholesterol concentration of 3.68 mmol/l is applied on pieces of membranes, followed by waiting a few seconds until the liquid was penetrated into the membrane. Then the humidified surface, which appeared to be the same on both sides of the membrane, was measured. In order to determine the influence of the viscosity, the same test has particular the influence of the viscosity, the same test has been carried out with water.

The experiments were carried out with membranes of type PS-11, obtainable from the firm X-FLOW B.V. at Enschede, which membranes were composed of polyether sulphone and polyvinyl pyrrolidone having a pore size of about 0.5 micrometer. The thickness of the membrane was 0.2 mm. The results are listed in table A hereunder.

TABLE A

| Test liquid | amount (l) | surface (mm$^2$) measurement 1 | measurement 2 | measurement 3 |
|---|---|---|---|---|
| A. Test- | 5 | 49 | 50 | 49 |
| serum | 10 | 101 | 101 | 99 |
|  | 15 | 150 | 148 | 151 |
| B. Water | 5 | 50 | 51 | 49 |
|  | 10 | 100 | 99 | 99 |
|  | 15 | 152 | 148 | 150 |

From this example it appears that the porosity of the membranes, and therefore the amount of plasma which may be absorbed, are sufficiently reproducable for carrying out quantitative measurements.

EXAMPLE II

A. Onto a hydrophilic microporous membrane of the type PS-11, see example I, having dimensions of 7 mm×25 mm on one side thereof there is applied a drop of blood obtained from a 45 year old man by finger puncture. After 1 minute a piece of membrane having dimensions of 7 mm×7 mm was removed therefrom by cutting, which piece was saturated with plasma. The membrane part to which the drop of blood was applied, was discarded.

The piece of membrane of 7 mm×7 mm was transferred into a cuvet which contained 1 ml of cholesterol reagent of the type Medela E 550-R, wherein the contents of said membrane has been washed out.

The test was carried out according to the known enzymatic coloric method at a wave length of 540 nm in a Vital Scientific Vitalab 10 colori meter, which was calibrated by means of a standard cholesterol-calibration serum of 3.68 mmol/l and 8.01 mmol/l, derived from R.I.V.M. under type A.

The cholesterol content of said blood was determined on a value of 5.2 mmol/l at a contents of the membrane of 5 microliters.

B. As a control of the test under A hereinabove blood was taken from the same person at the same moment by means of a vena puncture, followed by centrifugation of said blood and from the obtained serum there was 5 μl added to 1 ml of the same cholesterol reagent. Then the cholesterol contents of the serum has been determined similarly as disclosed in A above. The colorimetric measurement showed a cholesterol contents of 5.2 mmol/l.

C. From the serum obtained under B a drop has been applied to a membrane PS-11 having a dimension of 7×25 mm. This has been treated similarly as under A above. The measurement showed a cholesterol contents of 5.3 mmol/l.

EXAMPLE III

A. An asymmetric hydrophilic microfiltration membrane of the type PS-21, available at the firm X-FLOW B.V. at Enschede, which membrane essentially consisted of polyether sulphone and polyvinyl pyrrolidone and on one side it had a pore size of 0.5 μm and at the opposite side a pore size varying between 50 and 100 μm, and having a thickness of 0.5 mm, with its side having the smallest pores has been applied to a membrane of the type PS-11, which had a dimension of 11 mm×11 mm.

Onto the membrane PS-21 about 50 μl whole blood, obtained by finger puncture from a 38 year old man was applied. The particulate materials remained in the membrane PS-21, whereas the plasma penetrated very quickly (within a few seconds) in the membrane PS-11 thereunder. Then the membrane PS-21 has been removed and the membrane PS-11 was transferred into a cuvet containing 1 mm cholesterol reagent of the type Medela E 550-R, wherein the membrane was washed out.

At a membrane contents of 12 μl, the cholesterol content of the blood was determined on a value of 5.8 mmol/l.

B. As control 12 μl serum, derived from centrifugated blood, which was obtained by means of a vena puncture with the same person at the same moment, was directly added to a cuvet which contained 1 ml of the cholesterol reagent. This control test resulted similarly in a cholesterol content of 5.8 mmol/l.

We claim:

1. A process for the determination of constituents in body fluids which comprises applying a body fluid sample to a hydrophilic separator membrane having a plurality of asymmetric pores extending therethrough and having pore openings on first and second sides of said separator membrane which permit body fluids to pass through said pores while retaining particulate materials, said body fluid sample being applied to the first side of said asymmetric separator membrane in which the average size of the pore openings is larger than the average size of the pore openings on the second side of the separator membrane, collecting the separated body fluid passing through said separator membrane into a hydrophilic collector membrane having a defined pore volume so as to collect a determinable quantified amount of said body fluid, and analyzing for the constituents of said collected quantified body fluid.

2. A process according to claim 1, wherein the collector membrane contains a reagent which is reactive with a component of the collected body fluid.

3. A process according to claim 1 wherein the separator membrane contains a coagulation or hemolysis inhibiting agent.

4. A process as defined in claim 1 wherein said body fluid is whole blood.

5. A process as defined in claim 1 wherein the separator and collector membranes are prepared by fixing a hydrophilic polymer in or on a hydrophobic polymer material.

6. A process as defined in claim 1 or claim 5 wherein the size of the pore openings on the first side of the separator membrane are in the range of 10 micrometers to 1 millimeter and the size of the pore openings on the second side of the separator membrane are in the range of 0.2 to 5 micrometers.

7. A process according to claim 5 wherein the hydrophobic polymer is selected from the group consisting of polysulphone, polyether sulphone and polyether imide and the hydrophilic polymer is polyvinyl pyrrolidone.

8. A device for separating particulate materials from body fluids which comprises a holder containing a hydrophilic separator membrane having pores of asymmetric size extending therethrough and having pore openings on first and second sides of said separator membrane, a hydrophilic collector membrane having a determined capacity for collecting a quantified amount of body fluid, said collector membrane being in intimate surface contact with the second side of the separator membrane having pore openings of an average pore size smaller than the average pore size of the pores on the first side of the separator membrane, so that a quantified amount of body fluids passing through the separator membrane is collected by the collector membrane.

9. A device as defined in claim 8 wherein the collector membrane contains a reagent which is reactive with a component of the collected body fluid.

10. A device as defined in claim 8 wherein the separator membrane contains a coagulation or hemolysis inhibiting agent.

11. A device as defined in claim 8 wherein the size of the pore openings on the first side of the separator membrane are in the range of 10 micrometers to 1 millimeter and the size of the pore openings on the second side of the separator membrane are in the range of 0.2 to 5 micrometers.

12. A device as claimed in claim 8 or claim 11 including means for removing the collector membrane from intimate surface contact with the separator membrane.

13. A device as defined in claim 8 wherein the separator and collector membrane are prepared by fixing a hydrophilic polymer in or on a hydrophobic polymer material.

14. A device as defined in claim 13 wherein the hydrophobic polymer is selected from the group consisting of polysulphone, polyether polysulphone and polyether imide and the hydrophilic polymer is polyvinyl pyrrolidone.

* * * * *

UNITED STATES PATENT AND TRADEMARK OFFICE
CERTIFICATE OF CORRECTION

PATENT NO. : 5,240,862
DATED : August 31, 1993
INVENTOR(S) : DIRK M. KOEHEN and JOHAN J. SCHARSTUHL PAGE 1 of 2

It is certified that error appears in the above-indentified patent and that said Letters Patent is hereby corrected as shown below:

In the Abstract, line 3 should read "in said fluid"

Col. 1, l. 17, should read "body fluid migrate"

Col. 2, l. 7, correct the spelling of the word "materials"

Col. 2, l. 18, correct the spelling of "semi-quantitative"

Col. 2, l. 22, correct the spelling of "semi-permeable"

Col. 2, l. 24, correct the spelling of "semi-permeable"

Col. 2, l. 31, correct the spelling of "semi-permeable"

Col. 2, l. 40, correct the spelling of "semi-permeable"

Col. 3, l. 41, correct the spelling of "particles"

Col. 4, l. 14, correct the spelling of "reproduceable"

Col. 4, l. 56, take out the comma (,) after "already"

Col. 6, l. 44, should read "Under an"

Col. 7, l. 65, correct the spelling of the word "fact"

Col. 8, l. 59, correct the spelling of the word "removal"

Col. 11, l. 30, cancel the line

Col. 11, l. 33, should read "the type"

UNITED STATES PATENT AND TRADEMARK OFFICE
CERTIFICATE OF CORRECTION

PATENT NO. : 5,240,862
DATED : August 31, 1993
INVENTOR(S) : DIRK M. KOEHEN and JOHAN J. SCHARSTUHL It is certified that error appears in the above-indentified patent and that said Letters Patent is hereby corrected as shown below:

Col. 11, Table A, l. 42, under the heading "amount", the unit should read --µl--

Claim 13, l. 2, correct the spelling of the word "membrane$\underline{s}$"

Signed and Sealed this

Fourteenth Day of June, 1994

Attest:

BRUCE LEHMAN

Attesting Officer     Commissioner of Patents and Trademarks